United States Patent [19]
Szabo

[11] Patent Number: 5,954,640
[45] Date of Patent: Sep. 21, 1999

[54] NUTRITIONAL OPTIMIZATION METHOD

[76] Inventor: Andrew J. Szabo, 130 Washington St., Dobbs Ferry, N.Y. 10522

[21] Appl. No.: 08/671,413

[22] Filed: Jun. 27, 1996

[51] Int. Cl.$^6$ ............................................. A61B 5/00
[52] U.S. Cl. ................................. 600/300; 128/921
[58] Field of Search ................... 600/300, 301; 128/920, 921, 923, 924

[56] References Cited

U.S. PATENT DOCUMENTS

| | | | |
|---|---|---|---|
| 4,731,726 | 3/1988 | Allen, III | 600/300 |
| 4,954,954 | 9/1990 | Madsen et al. . | |
| 5,233,520 | 8/1993 | Kretsch et al. . | |
| 5,412,560 | 5/1995 | Dennision . | |
| 5,412,564 | 5/1995 | Ecer | 128/921 |
| 5,692,501 | 12/1997 | Minturn | 600/301 |
| 5,836,312 | 11/1998 | Moore | 128/921 |

*Primary Examiner*—Linda C. M. Dvorak
*Assistant Examiner*—Bryan K. Yarnell
*Attorney, Agent, or Firm*—Milde, Hoffberg & Macklin, LLP

[57] ABSTRACT

A method for proposing and providing nutritional supplementation for a person comprising the steps of receiving personal information, e.g., relating to health and diet, about the person, determining a health model for the person, determining an effect on the health model for at least two nutritional supplements, optimizing a proposed nutritional supplementation for the person based on the personal information about the person and effect for the at least two nutritional supplements, through employment of the health model, and outputting a proposed nutritional supplementation including amounts of at least two nutritional supplements. The method may also receive economic considerations, e.g., a budget, for the nutritional supplementation, and further optimize the nutritional supplementation based on the economic considerations.

41 Claims, 3 Drawing Sheets

NUTRITIONAL OPTIMIZATION METHOD

FIELD OF THE INVENTION

The present invention relates to the field of nutritional optimization systems and methods, as well as to apparatus for the analysis, storage and retrieval of nutritional optimization data and a system for delivering a nutritionally optimized product.

BACKGROUND OF THE INVENTION

It is well known in the art to analyze a diet of a mammal for typical macronutrients, such as carbohydrates, fiber, fat, protein, major vitamins and minerals. In fact, there is a well developed field of nutrition which seeks to employ medical and public health principles to determine an "optimal" diet. Further, total parenteral nutrition is known, wherein foods are determined and administered to a patient, often in a controlled environment. Infant formulas are also a known area of economic and dietary optimization based on public health and medical considerations.

Multivitamins are known, wherein a mixture of vitamins, minerals and cofactors are provided in a convenient dosage form. The levels of components are generally selected to be a significant portion of a recommended daily allowance (RDA) and up to about ten times the RDA. These multivitamins, however, are available in limited varieties, e.g., children's, women's, men's, and senior citizen's.

Of particular import in these many known systems is that these systems are not open to conjectural nutritional effects of components. Thus, if the effect of a component is not specifically known, these systems have no way to scientifically analyze its inclusion in a proposed optimized diet.

A known system, disclosed in U.S. Pat. No. 5,478,989, incorporated herein by reference, provides a computerized shopping cart for a supermarket which includes a bar code scanner, allowing typical UPC codes on food packaging to be read. A database of information about the food item may then be recalled, which may include labeling information. The consumer inputs personal information, and the retrieved information is presented in relation to the personal information of the consumer. This system, however, does not include an economic model, and does not relate to nutritional supplements for which no medical benefits are claimed. Further, this system does not make proposals, but rather returns processed information based on an input representing an item and the personal information.

SUMMARY OF THE INVENTION

The present invention provides an optimization of nutritional supplementation based on models that allow prediction of a change in health from an existing status, as a result of administration of a plurality of nutritional supplements. Relevant to various embodiments of the invention are activity of each nutritional supplement, desired change in status, toxicity and adverse effects of nutritional supplements, interactions between nutritional supplements and other factors, cost and economics of the nutritional supplementation, and risk, both positive and negative.

The present invention addresses the issue of nutritional supplements of incompletely or equivocally known value, and is thus not limited to predictions of the effects of unequivocally proven medical effects of supplements. In general, claims of medical benefit are not made for nutritional supplements, with the exception of known vitamins, minerals and bioavailable cofactors, and there is little standardization for dosage and regimens. As such, the database as to each of the factors in the optimization, with the exception of cost, may be partially undetermined. Thus, in contrast to known systems which operate on concrete data and established and accepted principles, the system according to the present invention operates to propose an optimization with incomplete or inconsistent data.

Another embodiment of the present invention employs a model of health of a mammal which encompasses both traditional nutritional analysis as well as unverified benefits of nutritional supplements for which no official or universally recognized standards are established. In fact, each individual may select a particular health model to employ, which may be different from or even partially inconsistent with other available or known health models. Thus, the individual is allowed personal choice of the model selected in the optimization.

The present invention also allows an optimization of nutrition and nutritional supplementation for a group of persons, such as a family. Thus, the optimization of the group health proceeds similarly to a public health analysis, e.g., the maximum good for the greatest number, while preventing detriment to the individual. However, this model operates on defined individuals, who preferably each have a health and personal information database record. The optional economic model, therefore, operates on the larger group rather than the individual person. In an analogous manner, an optimization may be created by the present invention for any delimited group, where that group's characteristics may differ from that of the "population" contemplated by a public health model. For example, a group of scouts on a camping trip will generally be expected to have similar activity and exercise levels, similar age and fitness, and therefore the menu for the group may be optimized based on a budget and health model. Parallel considerations would apply to food service in such institutions as school cafeterias, prisons, hospitals, welfare kitchens, or workplaces. The methods and apparatus according to the present invention allow particularized nutritional supplementation of the individual or group, to achieve an optimum health benefit. As noted below, the system may be integrated with various apparatuses to assist a consumer in shopping for foodstuffs and nutritional supplements.

A preferred embodiment of the invention employs an economic optimization of nutritional supplementation. Therefore, in addition to determining which nutritional supplements are appropriate, the cost of each component or the proposed nutritional supplementation as a whole is determined and used to achieve the maximum health benefit for given economic factors, such as a budget. Therefore, as a further aspect of this embodiment, the cost structure of combination supplements and quantity discounts are considered. In addition, third party health insurers or life insurers may provide payments, discounts or rebates for the proposed regimen. Where an economic model is not explicitly employed, a user may be presented with one or more proposals having differing nutritional supplement costs, which may then be selected by the user.

While the present invention encompasses the tenets of non-traditional medicine and nutritional supplementation, it does not eschew traditional health schemes. Thus, known diagnostic, analytic and prognostic indicators can be employed to determine an optimization of nutritional supplementation for a given individual. Further, certain patients are fragile, and therefore a risk of health deterioration due to supposed nutritional health optimization is considered. Therefore, an aggressive health optimization may be proposed for a healthy young individual, while a conservative approach may be proposed for an elderly patient with various ailments.

Further, the present optimization may be cognizant of medical, surgical or pharmaceutical treatments of a patient, as well as natural conditions such as menstruation or lactation, or disease, and determines or predicts any potential interactions between prescribed care and proposed supplementation in order to avoid adverse interactions or detrimental effect on the treatment regimen. Beneficial interactions are also cognized, and thus may be used to increase efficacy or efficiency.

Further, the present optimization may be cognizant of toxicity of the entire dietary and supplementary regimen, particularly in relation to the liver and kidneys, but also considering other organs and systems which may be stressed, including the heart, reproductive system and endocrine system.

The present invention may also provide a temporal optimization of nutritional supplementation, wherein diurnal, weekly, monthly and/or seasonal or life-cycle variations are considered and factored into the optimization scheme. Further, as a part of the cost optimization, dosing schedules and component half-lives may be considered in order to allow the most effective and most convenient nutritional supplementation. For example, the cost of a nutritional supplement generally is not solely related to the amount of a nutritional component in the supplement, and higher doses are generally less costly per unit than lower doses. On the other hand, higher purity components may be more expensive per unit dose, for example where the purification process is difficult. Such higher purity dosage forms may be desirable, for example where the impurities are harmful or have undesired effects, or where the shear volume of nutritional supplement is undesired. Thus, the proposed nutritional supplementation may include an analysis of dosage forms.

As used herein, nutritional supplements include foods, capsules, pills, powders, gums, and liquids, or other oral dosage forms which include known or quantifiable nutrients. Also encompassed are nutritional supplements delivered in any manner to the digestive system or intravenously, as well as nutritional supplements which are administered through other routes, such as through mucous membranes.

Often, nutritional supplements are provided in a form which includes excipients, impurities, or other components than the denominated nutritional supplement component. Therefore, another embodiment of the present invention analyzes, to the extent possible, the nature of the nutritional impurities or excipients, and include these components in the nutritional optimization.

In general, as stated above, macronutrient (foodstuff) optimizations are known, and the present invention may encompass this aspect of nutritional optimization as well. Thus, for example, an individual indicates his normal nutritional intake as an input to the system, which is to be supplemented or modified. The result of the optimization may therefore include a proposal to reduce intake of a supplement, macronutrient or foodstuff, as well as increasing or adding nutritional supplements. Thus, heavy consumption of milk may suggest lesser supplementation with fat soluble vitamins D and E, as well as calcium.

The present system provides an individually tailored proposal for nutritional supplementation or modification of intake. Being a proposal, and given the nature of mandates of dietary intake, the proposal may be accepted or rejected by the individual. Therefore, another embodiment of the invention involves an interactive process for arriving at a proposal, as well as a correction of optimization based on a deviation from a proposal. In this case, the cost optimization and risk analysis potentially play an important roles in a statistical analysis to arrive at a proposal. Since it would be expected that, except in the case of total parenteral nutrition, no absolute dietary schedule will be maintained, and further that it is primarily those individuals whose diets are most aberrant initially who are recalcitrant to change, the optimization proposal must include leeway for deviations.

Therefore, one embodiment of the invention provides an immediate feedback of a proposed nutritional supplementation based on an actual present status of a person, including recent meals and nutritional supplements, activity, health status and prospective events. This optimization may be provided through a hand held, pocket or bracelet (watch-type) device, personal computer, personal digital assistant (PDA), as a device which might be attached to or integral with a shopping cart, terminal to an on-line service, through the Internet (e.g., through a server or as a Java application), telephone with voice communication, kiosk, or centralized computer system. Therefore, a full featured system may be used to define an optimization, which may then be used to download an optimization to a portable or remote device. The programmed optimization may then be used to help keep the person "on track", and to report on an actual pattern of activity, diet and nutritional supplementation. While the portable or remote device may alter or reselect optimization continuously or often, preferably the optimization is performed infrequently, such as once per month.

Thus, a reoptimization may be performed periodically, e.g., monthly, or frequently, e.g., daily. The optimization procedure may also be provided as major optimizations, in which substantial changes to underlying models are implemented, and minor optimizations, where perturbations from a desired health status are corrected by nutritional supplementation according to a determined model.

A preferred embodiment includes an economic optimization because, without this factor playing an explicit role, the "more is better" theory may produce a proposal which is untenable. Known systems which attempt to optimize nutrition perform economic optimization in one of two ways. First, the public health model selects cost levels designed to do the most good for the most people. Some persons will receive a suboptimal dose, while others will receive little incremental benefit or even suffer toxic effects. Further, some persons will be asked to spend more than a reasonable amount, while others will have excess disposable funds without guidance as to how these funds should best be employed. Thus, the public health model does not account for an individual and his own specific factors, including budget. Second, an incomplete or limited economic analysis may be performed without the benefit of a linked health model. For example, an individual who visits a health food store and selects supplements performs a limited economic model, e.g., "that costs too much", in the selection of items for purchase. By linking the economic model with an individual health model, the benefits of a personalized proposal at acceptable cost is obtained. Further, by allowing a statistical error in the actual diet as compared to the proposed diet, the optimization may produce a better "real-world" result.

In operation, the system first obtains personal data about an individual. This may be obtained through automated data analysis, interview, survey, subjective analysis, laboratory testing, and the like. A database is provided with information about available nutritional supplements, including contents, price, and dosage form. A further database includes information, including risks and benefits, about constituents of nutritional supplements. A system, preferably a computerized algorithm, computes a health model of the individual based on the input information, as well as a desired budget. This model computes a present state of health, according to the available information, and determines a desired state of health, based on the maximum benefit for the available funds and the available nutritional supplements.

The resulting nutritional supplements, intended to help a mammal reach the desired state, along with suggested changes in the existing diet, comprise the proposal. In appropriate circumstances, activity and exercise may also be aspects of the proposal. The individual, however, need not accept the proposal, and may thus interact with the system to modify the proposal in specific aspects. These changes act as constraints for a secondary modification of the proposal. For example, a selected health model may suggest 300 mg of ascorbic acid (vitamin C) per day, in three doses. However, the individual may prefer 750 mg per day in three doses. Thus, the proposal is then updated with 750 mg per day in three divided doses as a constraint. The entire health model must be recomputed based on this constraint. In recomputing the model, the system further determines whether this constraint implies that a different model is more appropriate for implementation. In order to resolve this issue, the individual may be queried to determine the reason for the preference. If appropriate, hybrid models may be employed. The nutritional supplement proposal may thus include timing and frequency of dosage of the nutritional supplementation.

In theory, an economic based model may result in a highly skewed proposal, with high doses of relatively cheap components and without any expensive components. However, often, temperance and variety are desired, and thus amounts of some nutritional supplements are limited and others added, even though these result in reduced benefits according to a strict scientific analysis. Thus, a perceived benefit of a nutritional supplement may be in excess of a rational analysis of the potential benefit based on a review of existing scientific data. Thus, a health model may include an analysis of a perceived benefit of a component, rather than necessarily a scientific analysis. Further, it is noted that, in accordance with the scientific method of analysis of nutritional supplementation, studies may fail to show a benefit, or produce contradictory findings, even for nutritional supplements of real value. For example, ginseng is believed by many to be beneficial, but many scientific studies have failed to reveal a health benefit. This does not mean, however, that the proposed benefit of a component is not real. Another limitation of scientific methods is that they emphasize dose-response relationships over balance. However, a perception of an individual may be that supplementation of smaller amounts of many different components is preferable to megadoses of a small number of nutritional supplements. Another limitation of typical scientific studies is a difficulty in proving subtle long-term effects of small doses.

A further embodiment of the implementation of the present invention includes an apparatus for formulating nutritional supplements. Thus, based on the proposal, custom formulation may be provided to an individual. Alternately, standard dosage forms may be selected for the proposal.

A still further embodiment of the invention provides a vending machine or point of sale dispensing machine which formulates or combines pre-prepared dosage forms of nutritional supplements based on the proposed nutritional supplementation. Where the point of sale dispensing machine is in a public location, a limited interface may be provided, for example, a touchscreen and a magnetic stripe or smart card interface. Thus, a person previously registered with a central system may present to a kiosk or free-standing machine, and be identified by a card, e.g., a credit card or smart card. The card is used to call up a record of the person, which is then employed to generate a "welcome" screen for the person. Such a machine can also provide for custom packaging of a group of standard dosage forms of nutritional supplements.

Optionally, a user may be interviewed by or in the presence of a trained professional, with the data inputted or accepted in an objectivized format. Thus, with a trained professional, e.g., a doctor, nurse, chiropractor, social worker or nutritionist, the input of medical information, analysis of choices, selection of models, and approval of proposals may be facilitated. The interaction between user and professional may also be part of a consultation or treatment session, and the data entry shared with a medical records system. Thus, the nutritional supplementation system may be integrated into traditional medical care settings, and users who are in need of traditional medical care directed away from potentially inappropriate self-help paradigms.

After initialization of the system, e.g., identification of the person, the person may then interact with the system, for example through a graphic user interface with a touchscreen input. The graphic user interface may employ standard constructs, such as menus, icons, and dialogue boxes. The screen interface may also be customizable for the user, e.g., language, level of sophistication, preferences, etc. In conjunction with the interface, a database retrieval system may be provided to assist the person in making choices and selections. Thus, a search engine may be accessed, as well as pre-formed strategies for searching various topics. Where the system connects to an on-line service, or the Internet, so-called "spiders" may be employed to retrieve information of a class specified by the user without requiring explicit identification of each record. Further, so-called agents may be used to assist in interaction with the system. The agents may include, for example, aspects of the various selected models. The software described may be executed on a server, client or stand-alone computer. In particular, the optimization may be performed on a personal computer, with the resulting proposal printed for manual delivery or transmitted to a host system. The present invention therefore envisions electronic commerce where an order executing the proposal is transmitted electronically, with the resulting goods delivered through standard channels, such as mails, couriers and parcel post. The present invention also envisions execution of the software at or near a point of sale, with the goods delivered at or in close proximity to the terminal. Thus, the terminal itself may include a vending machine or be in a retail nutritional supplement sales environment.

The system thus seeks to determine, based on a set of personal preferences and constraints, as well as a health model and optionally a personal economic optimization model, an optimal proposal for nutritional supplementation. Public health concerns partially defer to individual health considerations. Further, absolute health mandates defer, within limits, to personal preferences and optionally cost tolerance.

In a typical application, a consumer initially identifies himself to a computerized system and undergoes an interview process. If the consumer is known to the system, i.e., has a database record, the prior history of the consumer is recalled. Otherwise, the consumer is processed as a new user. The system may also have or be granted access to medical records of the user. Based on the interview, information relating to the consumer, including present health status, dietary habits, medical treatments, activities, exercise and preferences are determined. Further, a health theory is proposed, based on responses to particular questions or scenarios.

An economic model is optionally formulated, which may be as simple as a daily, weekly or monthly budget for nutritional supplements, or a more complicated analysis including normal food intake and expected health benefits. The economic model may also include expectation of third party benefits, such as payments, discounts, subsidies, rebates, insurance or copayment by health or life insurance organizations, health maintenance organizations, prepaid provider organizations, or others. In fact, these third parties may grant economic benefits which are dependent on a correspondence between an organizational health theory and a proposed health theory. Thus, the third party may skew the proposed nutritional supplementation based on selective economic benefits. It is also noted that economic constraints may change over time, and therefore a reoptimization may be required on each such change.

Based on an estimation of the present status of the consumer, the system then seeks to propose specific changes and nutritional supplements, in accordance with the health theory, expressed preferences, and optionally within the constraints of the economic model, to maximize the expected benefit to the consumer. The consumer then interacts with the system to "tune" the proposal based on personal preferences. After acceptance, the consumer may then execute the proposal by purchasing the recommended supplements. As stated above, the purchase system may be linked to the terminal, in communication with the terminal, or completely separate.

Over time, the system may determine whether the proposals are achieving a desired effect, to the extent that this is determinable. For example, medical tests or diagnoses, or subjective responses to inquiries, may be used as feedback data. Where appropriate, the system may be interfaced with diagnostic or exercise equipment, to obtain objective data. If the effect is as expected, then the proposal is reinforced. If the effect differs from the expected effect, then the proposal is reoptimized based on the feedback. Accordingly, if the consumer is a high responder to a nutritional supplement, the amount of the supplement may be increased as compared to other components. Alternately, the amount may be reduced, if the increased response is undesired or unnecessary. In an economically optimized system, economic resources may be freed for other nutritional supplements. Thus, the system may employ a closed loop feedback input with periodic reoptimization.

If a consumer alters his preference, or the health theory is altered, either by selection of a new theory by the consumer or an alteration in the theory based on new evidence, the subsequently generated proposals may also be altered. However, the system will continue to rely on closed loop feedback to personalize the proposals.

The personal interview will acquire data about the consumer's nutritional background, sex, weight, age, ethnic background and familial health risk factors, environmental and behavioral health risk factors, allergies, medical conditions, drugs currently being taken, treatments and responses, activities, exercise, as well as subjective factors.

In order to further evaluate the consumer, it may also be desired to obtain data relating to diagnostic tests on the consumer, such as blood tests for levels of specific micronutrients or indicative of nutritional status.

In order for the economic optimization according to the preferred embodiment to be fully effective, a complete and accurate database of the costs of various options must be available. As such, one embodiment of the invention provides an electronically accessible database of nutritional supplement content and cost information. The database may also include information about the normal food budget of the consumer, since a change in the food budget may result in a change in the nutritional supplement budget.

The database of costs may be integrated with an inventory management system for a retail, wholesale or mail order nutritional supplement vendor, and may be accessed by, for example, by SKU or bar coded UPC symbols. Thus, while shopping, a user may be able to determine or test the effect of a particular proposed purchase on the optimization.

The health model or theory is a set of rules, formulae, statistics and factors which allow analysis of the present health status of the consumer as well as a hypothesized change in status due to one or more nutritional supplements. Linked to this health model are activity and toxicity models for the nutritional supplements, so that the type and amount of nutritional supplements to be proposed may be analyzed in conjunction with the present status of the consumer. In particular, the activity model proposes a benefit of a nutritional supplement, while a toxicity model compels a limitation in dose. The activity and toxicity models may be combined into an efficacy model. Where the individual models do not explicitly account for interactions with other factors, models, and nutritional supplements, a separate interaction model may be provided to inform the consumer of potential interactions and seek to prevent hazards or inefficiencies, and to determine whether beneficial interactions are present or may be increased, for example by combining magnesium and vitamin D. Another example is the ability of ascorbic acid to degrade nitrosamines, which form from nitrites in foods, for example preserved meats and smoked fish. Thus, the nutritional supplementation optimization may propose that orange juice, a food, be consumed when lox and bagels are also consumed. Thus, the proposal is not limited to nutritional supplementation with micronutrients alone.

The present system may also include a further related concept, a model for optimization of health, which differs from the health model by allowing statistical analysis of risks and benefits, as well as contingent benefits.

Thus, a number of models operate simultaneously to achieve a result, i.e., a proposal. First, the health model defines the status and proposed status of the consumer. Second, the efficacy models define a change in state with respect to amount of nutritional supplements. The efficacy models are separated from the health model to the extent desired so that each may be modified separately to include new information. Third, the optional economic model limits the optimization to affordable levels, and serves higher purpose as well. The implementation of an economic model facilitates economic efficiency by allowing providers to seek cost effective nutritional supplements, even if this effect is somewhat delayed. The optional optimization of health model seeks to compensate for statistical risk and benefit, which may be independent from the health model or efficacy models themselves.

While the optional economic model may be relatively static, this model may also be more dynamic, and include the concepts of a "sale", discount coupon, incentives, quantity discount (individual component or gross order), handling, transaction costs and service charges, negotiations with the vendor, or other known economic perturbations or corrections. Further, as stated above, the economic model is subject to perturbation by the influences of third party payers. While the health model will generally not allow a third party to compel supplementation with an undesired nutrient, the economic model does weigh in favor of the subsidized nutritional supplements where these are beneficial.

In practice, these models are preferably provided as modular objects in a computer system, allowing one object to be substituted, altered or updated without simultaneously requiring consideration of corresponding or compensatory changes in other models which are not dependent on the changed object. Of course, the resulting optimization is a dependent object and must be recomputed after a change in a parent object. Each model therefore includes a set of formulae or parameters, which may be evaluated in context. The evaluation is a statistical or multifactorial optimization to determine a best proposal. As stated above, based on external inputs, factors of the model may be constrained. Further, closed loop feedback may be used to update or personalize the model for more accurate determinations.

The models or modeling system may also include neural networks or fuzzy logic paradigms. A neural network system is advantageous, for example, where a model may be expressed as a set of neural network weights, and therefore computing an optimization requires evaluation of the neural network. Preferably, the model is modular, with portions being separately evaluable and substitutable. Thus, the model may be formed of a set of modules, representing aspects to be optimized. A fuzzy logic system may be advantageous where semantic expressions may be used to describe a relationship, and where a precise logical statement of the relationship is difficult to determine or evaluate. A neural network is generally created by an iterative training process based on empirical data in a training process, while a fuzzy logic system is generated as a set of explicit rules in a programming process. Neural networks and fuzzy logic systems may be adaptive, i.e., changing over time based on feedback of an actual effect, to better predict how a nutritional supplementation may achieve a desired effect.

The system according to the present invention may also be employed with patients, i.e., persons under medical care for a disease. Thus, under such circumstances, the health model may particularly include a model of a disease, with the parameters of the proposal reviewed by a medical practitioner prior to implementation. Thus, for example, the system may be employed to optimize a total parenteral nutritional program for a patient. In this case, however, an economic optimization may be excluded or play a lesser role due to the high cost of medical interventions and the possible role of a hospital pharmacy or pharmacist. Even where total parenteral nutrition is not the desired result, a patient under medical care may benefit from the proposal. It is noted that where a medical professional makes the decisions, the health model will generally be conservative, i.e., employing accepted scientific theories and relationships, while the health optimization will also be conservative, e.g., "low risk". On the other hand, in some such cases, the efficacy models chosen may be very aggressive, in view of the medical supervision and the availability of close monitoring. Thus, the proposed doses may be closer to those at which toxic or adverse effects may be seen.

In forming the health models, as well as the other models, the necessary data need not be inputted as specific rules.

Thus, the models themselves may be adaptive based on the experiences of individual users or groups of users. Therefore, an objective and subjective feedback to the system may be used to improve the models and allow the predictions based on the models to more accurately reflect true consumer experience. As stated above, neural network technology and other adaptive paradigms may be employed to dynamically improve the models though use and feedback. Preferably, the raw data from users are not used directly to update the models, because this may lead to anomalies and subjective skewing. Rather, a filter is applied, preferably in the form of a trained person, to review the feedback data to determine the nature of the adaptation to be implemented and to control the process. Automated systems may also be used. Alternately, the feedback may be separately analyzed, and used as a basis for allowing consumers to select a different model, which may be perceived as more appropriate. For example, if a consumer experiences an undesired side effect from a particular nutritional supplement, the consumer may review information relating to others who consume the specific nutritional supplement, or others who suffer the same undesired side effect. This will allow the consumer to benefit from the experiences of others to potentially allow a change in nutritional supplementation to avoid the side effect. As another example, where the optional economic model is not a fixed budget for a limited period, the actual experiences of users or the specific consumer, including missed doses, change in diet, weight loss or gain (potentially resulting in dose changes over time), change in body fat content (potentially resulting in desired changes in fat soluble or water soluble nutritional supplements), and other factors may be used to more accurately match the nutritional supplementation proposal to the economic limitations.

The proposal need not be limited to nutritional supplements, and therefore changes in diet, activity or exercise may also be included in the proposals. It is noted that great changes in diet, activity and exercise are difficult to effect, and therefore such proposals may be of limited benefit. In fact, since non-compliance rates are expected to be high, an optimization based on a proposal requiring distinct efforts is likely to be rejected or ignored. On the other hand, simple changes in diet, which are likely to be adopted, may be very efficacious. Thus, on a pragmatic basis, the proposal preferably emphasizes small dietary changes and a regimen of pills and/or supplements, even where an equivalent change might be possible through extensive dietary modification or restriction. The user may therefore weight a relative expected importance of normal diet as compared to nutritional supplements.

Once a proposal is accepted, the system preferably has a link to a system for ordering nutritional supplements recommended in the proposal in standard packaging. Thus, according to the preferred embodiment, the economic model database system may include a link to an on-line ordering system from a nutritional supplement supplier. Alternately, the nutritional supplements may be individually formulated for a consumer from standardized ingredients. The proposal, once accepted may be directly entered into an ordering system, transmitted through an on-line service, e-mailed, printed, or directly filled as an order. Alternately, various supplements may be convenience packaged by daily dose.

Where the transaction occurs through an electronic medium, e.g., the Internet, the payments may involve traditional means, such as credit cards, or may involve newer systems for electronic commerce. Where sensitive medical or accounting information is transmitted through a public medium, it is preferably encrypted, such as with an RSA public key/private key algorithm, the PGP algorithm, or other encryption technique to prevent interception and ensure authenticity.

It is noted that often consumers will have a present regimen of nutritional supplements, possibly with existing inventory. In this case, assuming the consumer preference is to continue the existing regimen, the regimen will act as a constraint or soft constraint on the optimization, and the system will propose additional nutritional supplements and possibly modifications of the regimen. For example, where an existing regimen provides too much of a nutritional supplement according to a health model, the proposal may recommend lowering intake of that nutritional supplement. Where a constituent is inconsistent with the health model, the proposal will exclude that constituent. For example, a high iron intake might be inconsistent with an antioxidant health model, other things being equal. On the other hand, where an available constituent substitutes for an unavailable, though potentially preferable constituent, the optimization allows ingestion of an effective amount of the available constituent until the supply is exhausted, at which time the constraint is removed.

As an adjunct to selection of a health model, the system may also include educational features to inform the consumer about health, nutritional supplements in general, or specific nutritional supplements. Thus, a database entry may be provided for each nutritional supplement with both cost information as well as educational information. Further, a data retrieval system may be available to allow a consumer access to the information in a nonpredetermined manner. This educational information may also be used to guide the process of selecting a health model and identifying and analyzing risks for the health optimization model. The database may be provided locally or through an on-line or Internet based service. Further, searching capabilities may employ typical Internet searching techniques, for example to retrieve Usenet messages or world wide web pages.

Where educational information is provided, information may generally be segregated into two different categories. First, mainstream science published in peer reviewed journals represents a high quality source of information. However, such information may be delayed by the peer review process or the underlying studies may be prolonged. On the other hand, non-peer reviewed information and non-mainstream journals may develop hypotheses which require years of clinical testing in order to pass muster under the peer review process. Thus, while non-peer review information may be less trustworthy, it may be important and suggestive nevertheless. Further, the mainstream scientific community does not always address nutritional supplements in a timely manner, and therefore the non-peer review or non-mainstream publications may be the sole source of information or suggestion relating to certain types of nutritional supplements. The system may also be used to present topics of dissent and debate, which may form the essential differences between health models, and thereby present the distinctions and allow informed selection of a desired health model.

This distinction is also drawn elsewhere in the optional optimization process. The health optimization model factors in risk tolerance as a separate factor. Thus, a consumer with high risk tolerance might give greater emphasis to alternative medicine concepts than a lower risk tolerance consumer. This risk tolerance may be explicit, i.e., a person who expressly desires a higher risk (and higher potential reward) proposal, or implicit, i.e., a person who is healthy and can tolerate adverse effects better than an ill or fragile person.

On one hand, a Japanese user would likely find comfort in a traditional Japanese health model, which in western medicine is considered "alternate". On the other hand, an orthodox American medical practitioner using the nutritional supplement optimization system is unlikely to adopt substantial contributions from alternative medicine sources.

In order to avoid providing medical advice, which may permissibly be provided by a licensed physician, the system may instead provide access to the actual studies and works of authorship, without editorialization. Thus, the system may include a mass database of selected references which may inform the user of the risks and benefits of a given nutritional supplement, as well as aspects of a health model. Likewise, where official government advisory information exists, this information may be presented to the consumer. For example, alcoholic beverages in various forms may be considered beneficial in moderate amounts, yet toxic and addictive in higher doses, and pose substantial risks while driving or operating machinery. Therefore, alcohol products are accompanied by a warning. This warning, as well as various studies which support the use or abstention from use, may be available for review by the consumer. Thus, an herbal extract in alcohol may include a significant dose of alcohol with an effective dose of the herbal ingredient. Whether this alcohol is considered toxic or beneficial may depend on the health model chosen and also the contemplated activities of the consumer.

The interface to the system is preferably an interactive graphic user interface, allowing the consumer to make incremental selections and make modifications to selections during a session. The use of screen buttons, hot links, menus, dialogue boxes and other typical graphic user interface elements is therefore preferred. Through use of the system, the preferences of the user may be determined, and present further data and selections based on the determined preferences. Such a learning interface may allow efficient interaction between the machine and user. The system may be, for example, a Pentium® personal computer, Apple Power PC®, UNIX system, or other known type of computer system. The operating system is, for example, Windows for Workgroups 3.11, Windows 95, Windows NT, Macintosh Operating System, SunOS, Netscape/Java, or other known type.

While the various models seek to optimize health under the various constraints and inputs, a separate function is preferably provided to confirm that potentially dangerous or undesirable amounts or combinations are not proposed or selected. For example, excess amounts of fat soluble vitamins are to be avoided, and the calculations should encompass both the nutritional supplementation as well as the dietary load.

Preferably a proposal is accompanied by a statement or warning of potential or common side effects or adverse effects relating to the components of the proposal and the dosages and dosage forms proposed. Thus, a tailored screen output or printout specific for the user, which may specifically refer to the user's medical history or susceptibilities, is generated. During an encounter with the system, the user may be interviewed for serious or common effects, and warned to seek medical attention if an effect so warrants.

The system may reside on a local computer, network, client-server environment, on-line service, the Internet, or in other types of environments. Preferably, the consumer interacts with a terminal which has access to a remote database which includes model components, so that each terminal need not include the entire database. However, it is also possible to load the databases in a storage medium, e.g., CD-ROMs, so that a computer network is not required. These CD-ROMs would likely require periodic updating, for example, with changing economic and scientific information. The product information and economic information database together comprise a form of nutritional supplement catalog with current market prices, from which orders may be reliably produced.

BRIEF DESCRIPTION OF THE DRAWINGS

The preferred embodiments of the invention will now be described with respect to the figures, in which.

DETAILED DESCRIPTION OF THE PREFERRED EMBODIMENTS

Figure 1:
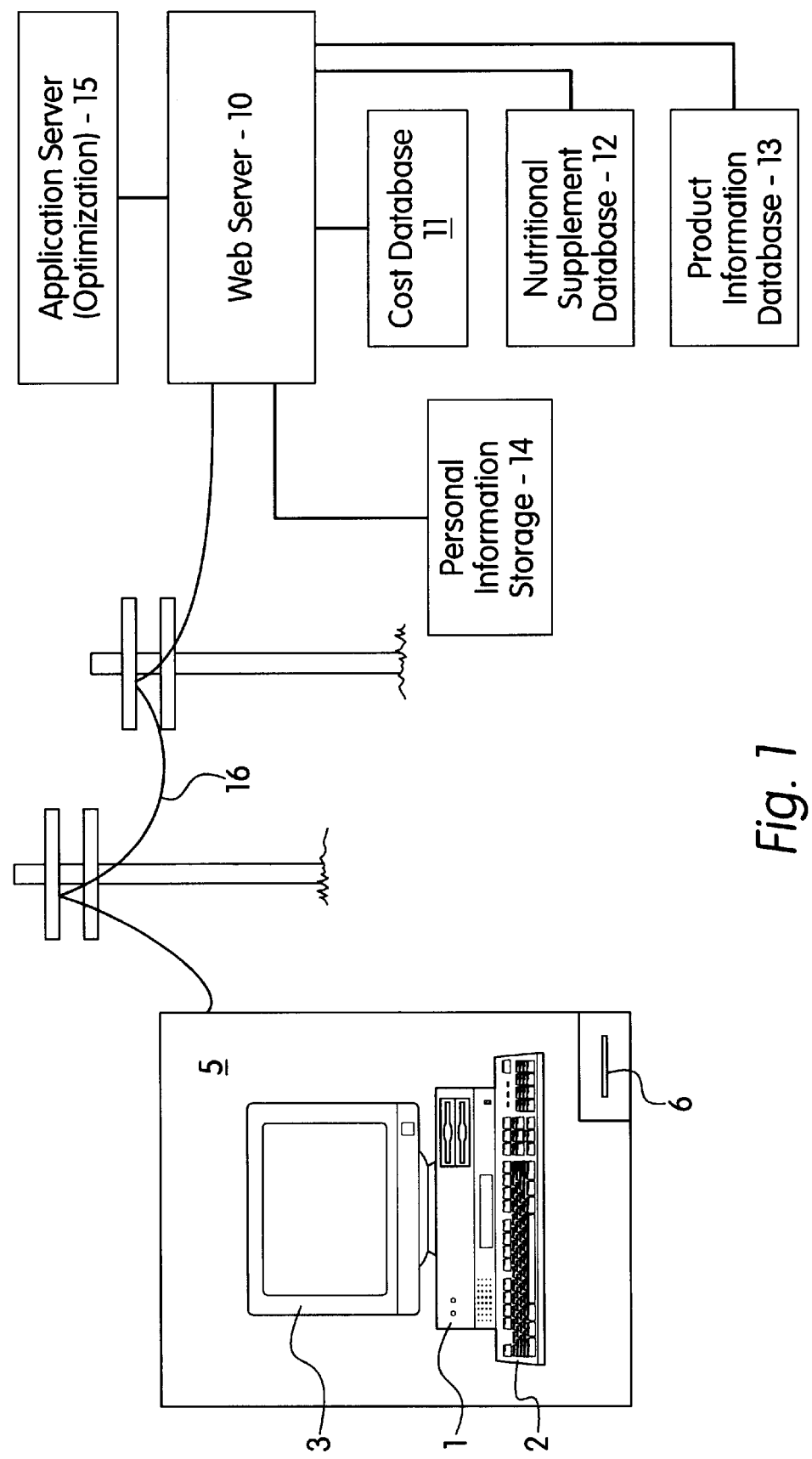
FIG. 1 shows a schematic view of a client server system for interacting with the optimization system according to the present invention.

A computer system is provided in a client-server environment. As shown in FIG. 1, a client system 1 includes a human interface, having a keyboard 2 or human voice auditory input, touchscreen 3, and video display 4 in a kiosk 5. The client computer is a Pentium® PC running Windows 95 and Netscape 3.0/Java. A hardcopy output device 6 (hidden in the drawing) is also present, e.g., a printer. The server, which is a Sun web server 10, stores the databases for cost 11 and nutritional supplement information 12, as well as the modeling information 13, and includes an application server 15 to evaluate the models and generate a proposal. Personal information is stored in a storage system 14, including health profiles, personal preferences, selected models, and other pertinent data. The client and server are linked by a network 16, e.g., TCP/IP over PPP dial up lines through the Internet, or over Ethernet, ISDN, Frame Relay, or other known means. The server 10 may also be linked to other systems, e.g., for deriving demographic information about registered persons for, e.g., targeted marketing.

Figure 2:
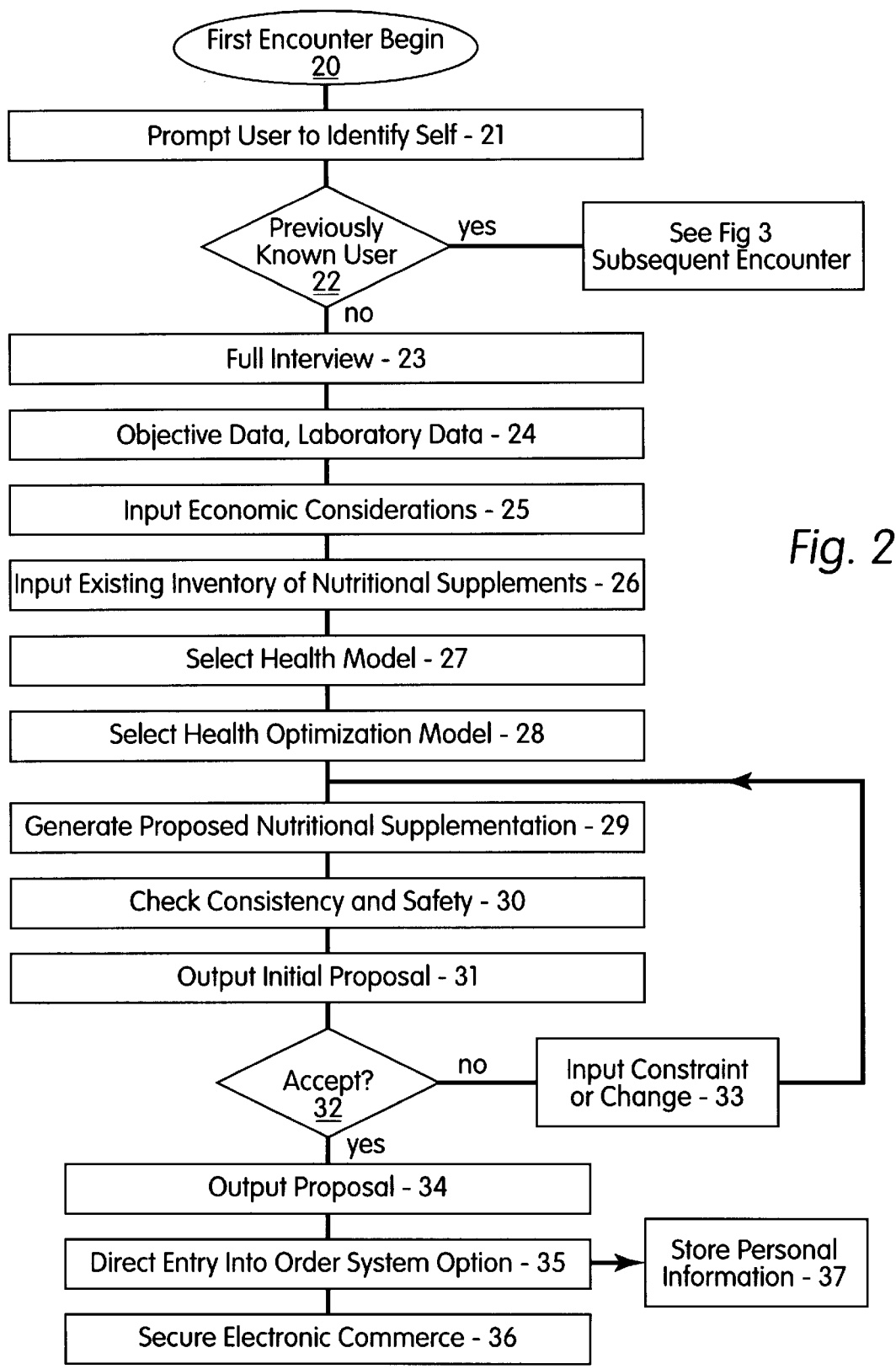
FIG. 2 shows a flow chart for processing a new user according to the present invention.

As shown in FIG. 2, the user is prompted to input various information, first identifying himself 21. If the user is previously known to the system 22, the prior data is retrieved 47 from the personal information storage 14 and employed, and the user need only update information 41, including any change in health status, diet, non-compliance with prior proposal, weight, diagnostic tests, preferences, or economic constraints. Of course, the user may also edit or change any prior information 42, which is entered 43, then verified 44, and finally saved 45. However, safeguards are placed to prevent intentional deception of the system to force an unsafe or unwise proposal 46, by placing risk limits and noting unexpected changes in data. Safeguards are also placed to prevent unauthorized intrusion into an individual's personal information records.

Where a novice user first uses the system, a full interview 23 is required. This interview acquires, where voluntarily provided, the user's nutritional background, sex, weight, age, ethnic background and familial health risk factors, environmental and behavioral health risk factors, medical conditions, treatments and responses, exercise, as well as subjective factors. Optionally, laboratory diagnostic information 24 may be obtained, such as blood tests for specific micronutrients and indicative of nutritional status, as well as other objective data.

Economic constraints or considerations 25 are received, e.g., a budget, for expenditures on nutritional supplements. Generally, this comprises an explicit input, but may be derived from other available information. Further, the economic constraints may be flexible, encompassing not only the nutritional supplements, but also dietary expenditures as well.

The user may also input an existing inventory 26 of nutritional supplements and optionally their acquisition cost. Otherwise, replacement cost is used to value the inventory.

A database is provided including cost information 11 for various nutritional supplements, and optionally specific information about the various nutritional supplement choices 12, such as contents. A further option is to provide differing databases from differing vendors, allowing a user to select a vendor of choice.

At least one health model is provided which determines an optimum change in nutritional and health status 13 for the user based on acceptable changes in diet or lifestyle. Included in these changes are nutritional supplements. This model comprises a large set of formulae which represent a health status of the user, as well as models of change in health status. Each health model includes efficacy modeling for a set of nutritional supplements, as well as interaction modeling for diet, nutritional supplements, pharmaceuticals, and other factors. Thus, in this case, the health, efficacy and interaction models are unified into a single model. The user must select a health model 27 from the available choices, or may optionally hybridize existing compatible models.

Finally, a health optimization model 28 is selected which modifies the health model output based on the concept of risk and benefit. Thus, a user indicates explicitly a subjective risk tolerance, while implicit determinations of objective acceptable risk are also determined. This model is statistical in nature, and seeks to alter the aggressiveness of the proposal based on the models. It is noted that the aggressiveness weighting relies on the underlying health model. If a user seeks moderate aggressiveness in nutritional supplementation, but not necessarily high risk, then a different health model is preferably adopted which proposes the desired regimen. Generally, it would be strongly suggested to users to avoid high risk or very aggressive models except under professional supervision.

In generating the proposed nutritional supplementation 29, it is noted that the various models may have global minima or maxima and local minima or maxima, and therefore known searching algorithms may be employed to select a preferred "operating point", i.e., to optimize the proposal. Further, it is also noted that full compliance is rarely obtained, so that the models or the health optimization model may precompensate for an expected degree of non-compliance. This expected degree of non-compliance may be estimated or based on subjective data or retrospective compliance data.

The proposal is also subject to a consistency and safety checker 30, which seeks to prevent mistake, interaction, or abuse of the system. Thus checker operates outside of the other optimization models and independently checks a proposal for likely error or difficulty.

The system calculates an optimized proposal and outputs it to the user 31. The user is given the opportunity to review the proposal 32, and may alter aspects of it as desired.

The use may modify the proposal 33 with a firm constraint of a particular type, and/or a flexible "counterproposal" with respect to one or more components of the proposal. The alterations are then again processed and optimized, to yield a new proposal. The process repeats until the proposal meets the desires of the user. However, the consistency and safety checker prevents an unsafe or unwise proposal from being generated, at least without a warning.

Figure 3:
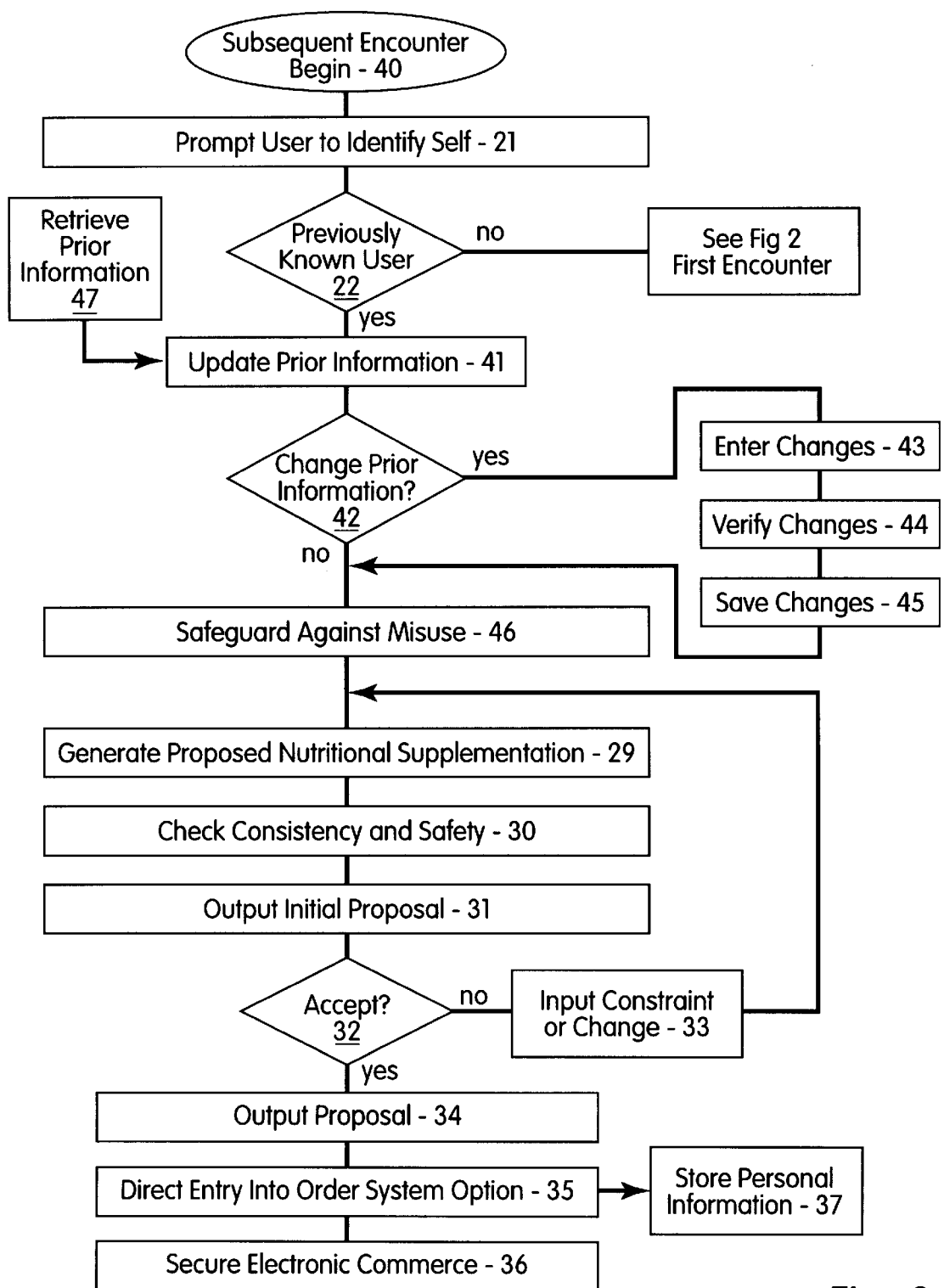
FIG. 3 shows a flow chart for processing an experienced user according to the present invention.

When accepted by the user, the final proposal is output 34, for example printed. Upon final approval, it may be directly forwarded for order processing to a vendor 35. Where the vendor is remote from the user, a secure electronic commerce system is employed 36. Any data input or modified by a user is stored 37 in a personal information database 14. While FIGS. 2 and 3 show the storage 37 occurring near the final steps of the transaction, the data may be stored at any time and preferably is at least temporarily stored as entered to prevent data loss in case of an interrupted session.

In a simplified but specific example, a consumer is a healthy 30 year old male with a balanced unsupplemented diet which meets the USDA Recommended Daily Allowances. The consumer selects an "antioxidant" health model, in which antioxidants are proposed to limit environmental toxins, limit ischemic damage due to hypoxia, and various other reputed effects. The consumer also selects a budget of $2.50 per day.

According to this model, Vitamin C, Vitamin B mixtures, Vitamin E, glutathione, as well as botanical polyphenols are considered advantageous. It is noted that glutathione and Vitamin E have caloric content, and thus, where the amounts given are significant, a reduction in normal dietary intake to compensate should be proposed.

Vitamin C is inexpensive, and often used as a filler and antioxidant in other vitamin mixtures. Thus, the vitamin C dose is maximized to subtoxic levels, generally 1500–2500 mg/day in divided doses. Vitamin B mixtures are also relatively inexpensive, and generally have a low cost at levels which avoid significant side effects. Vitamins B and C are often combined in economical dosage forms. Vitamin E is economically available, but is fat soluble, and thus the dose may be limited to about 500 IU per day. Thus, the vitamin B, C and E supplements are proposed at a reasonable "maximum" dose, leaving a significant portion of the budget remaining, e.g., about $2.25 per day.

Glutathione, while considered by many to be highly efficacious, is expensive, and thus is a cost limiting item in the optimization. Likewise, botanical polyphenols as extracts or concentrates are also considered efficacious but are costly. Therefore, one proposal might suggest that the consumer alter diet to obtain the botanical polyphenols as part of the normal diet, so that the remainder of the budgeted portion may be allocated to glutathione supplementation. Alternately, a proposal might suggest both glutathione and polyphenol nutritional supplementation in amounts proportionate to putative benefit per unit cost, to disburse the remaining budget. Thus, if glutathione is $2.50 per gram and considered to have 0.7 health benefit units per gram, and polyphenols are $20.00 per bottle of 30 100 mg capsules with 0.2 health benefit per capsule and $30.00 per bottle of 30 250 mg capsules with 0.35 health benefit units per capsule, the resulting optimization would propose one 250 mg capsule of polyphenols and 500 mg of glutathione per day. Note the drop in incremental efficacy of polyphenols according to the model and the effect of discrete dosage form availability.

In this particular case, the health model proposes an economically optimized nutritional supplementation with vitamins B, C and E as well as glutathione and polyphenols. This is, of course, a simplified example having a limited number of choices, and an actual system would have a plurality of models and a large selection of nutritional supplements available.

If the user were to seek to constrain the proposal to 10,000 mg vitamin C per day, the cost optimization might change slightly, but the consistency and safety checker would block the proposal or place a warning that such a high dose may be dangerous, e.g., renal calculi or rebound scurvy.

After the proposal is accepted, the server receives notification and payment authorization, such as from a credit card, and an order is entered with the vendor. A confirmation slip may be printed locally. The order is then processed by the vendor and shipped to the user. If a third party payor subsidizes this nutritional supplementation regimen, the order or information relating thereto may be forwarded to the payor for processing.

One month later, for example, the user may return to the kiosk 5 or other user interface system. At this time he identifies himself, and his records are retrieved. When queried about his current health status, for example, he notes objectionable skin flushing and lightheadedness after taking the water soluble vitamins. The system identifies this problem as being related to niacin flushing, and alters its proposal to a reduced flushing vitamin B (niacin) supplement formulation, for example a niacin and inositol mixture. This formulation is more expensive, and thus causes a reallocation of funds in the economic optimization. For example, less glutathione is provided.

In this case, the proposal does not identically correspond to readily available standard dosage forms of the nutritional supplements. However, a custom mixture remains an alternative. In this case, capsules containing the glutathione alone in a precise dosage, or combined with other nutrients, are custom made in sizes which correspond to the desired dose. While such custom mixture may entail a higher incremental cost than standard doses, for costly ingredients such custom mixtures may meet the requirements of the proposed nutritional supplementation better than other alternatives, and they also may provide a greater convenience utility versus ingestion of numerous pills or capsules.

Having illustrated and described the principles of the invention in a preferred embodiment, it should be apparent to those skilled in the art that the invention can be modified in arrangement and detail without departing from such principles. For example, discrete or integrated components of various types may be employed for the various parts of the apparatus, as is known to those of skill in the art. Features of the invention shown in software may also be implemented in hardware.

What I claim is:

1. A method for proposing nutritional supplementation for a person comprising the steps of:
   (a) receiving health and nutritional status information relating to a person;
   (b) providing information relating to a plurality of available nutritional supplements, the information comprising contents and cost;
   (c) determining economic constraints for the nutritional supplementation of the person;
   (d) optimizing a proposed nutritional supplementation for the person based on the health and nutritional status information, economic constraints and nutritional supplement information to improve a predicted health status of the person by nutritional supplementation with a plurality of nutritional supplements; and
   (e) outputting the proposed nutritional supplementation including amounts of the plurality of nutritional supplements.

2. The method according to claim 1, further comprising the steps of determining a risk tolerance of the person and further optimizing the proposed nutritional supplementation to achieve a maximum benefit within the determined risk tolerance.

3. The method according to claim 1, further comprising the step of analyzing a proposed nutritional supplementation for health safety.

4. The method according to claim 1, further comprising the steps of receiving feedback from the person relating to the proposed nutritional supplementation and reoptimizing to generate a revised proposed nutritional supplementation.

5. The method according to claim 1, wherein the economic constraints comprise a budget.

6. The method according to claim 1, wherein the information relating to a plurality of available nutritional supplements comprises records of a stored database.

7. The method according to claim 6, wherein the database is remote from the user.

8. The method according to claim 1, further comprising the step of providing a plurality of potential optimization procedures and selecting at least one of the optimization procedures for optimizing a proposed nutritional supplementation for the person.

9. A method for proposing nutritional supplementation for a person comprising the steps of:
  (a) receiving health and nutritional status information relating to a person;
  (b) providing information relating to a plurality of available nutritional supplements;
  (c) optimizing a proposed nutritional supplementation for the person based on the health and nutritional status information and nutritional supplement information to improve a predicted health status of the person by nutritional supplementation with a plurality of nutritional supplements;
  (d) outputting the proposed nutritional supplementation including amounts of the plurality of nutritional supplements as a proposal; and
  (e) transacting a sale of at least one proposed nutritional supplement with the person.

10. The method according to claim 9, further comprising the steps of receiving economic considerations from the person and optimizing the proposed nutritional supplementation further based on the economic considerations.

11. The method according to claim 10, wherein the economic considerations comprise a budget.

12. The method according to claim 9, further comprising the steps of receiving feedback from the person relating to the proposed nutritional supplementation and reoptimizing to generate a revised proposed nutritional supplementation.

13. The method according to claim 12, further comprising the step of analyzing a proposed nutritional supplementation for health safety or consistency.

14. The method according to claim 9, wherein the information relating to a plurality of available nutritional supplements, the information comprising contents and cost are stored in a database.

15. The method according to claim 9, further comprising the step of providing a plurality of potential optimization procedures and selecting at least one of the optimization procedures for optimizing a proposed nutritional supplementation for the person.

16. The method according to claim 9, wherein said sale comprises an electronic data transmission between a client system and a server system.

17. A method for proposing nutritional supplementation for a person comprising the steps of:
  (a) receiving health and nutritional status information relating to a person;
  (b) providing micronutrient information relating to a plurality of available nutritional supplements;
  (c) providing at least one optimization procedure for optimizing a proposed nutritional supplementation for the person based on the health and nutritional status information and nutritional supplement mironutrient information to improve a predicted health status of the person by nutritional supplementation with a plurality of nutritional supplements;
  (d) peforming one or more step selected from the group consisting of:
    (1) selecting one of a plurality of proposed optimization procedures for optimizing a proposed nutritional supplementation for the person; and
    (2) providing feedback from the person relating to the proposed nutritional supplementation and reoptimizing based on the feedback to generate a revised proposed nutritional supplementation; and
  (e) outputting the proposed nutritional supplementation including amounts of the plurality of nutritional supplements as a proposal.

18. A computer readable medium, having recorded thereon a series of computer implemented instructions for controlling a computer to execute the method according to claim 17.

19. The medium according to claim 18, the method further comprising the steps of generating a graphic user interface and interacting with the person through the graphic user interface.

20. The medium according to claim 18, the method further comprising the steps of communicating between a client computer in proximity to the person and a server through a computer network.

21. The method according to claim 17, further comprising the steps of receiving economic considerations from the user and optimizing the proposed nutritional supplementation further based on the economic considerations.

22. The method according to claim 21, wherein the economic considerations comprise a budget.

23. The method according to claim 17, further comprising the steps of receiving feedback from the person relating to the proposed nutritional supplementation and reoptimizing to generate a revised proposed nutritional supplementation.

24. The method according to claim 17, wherein the information relating to a plurality of available nutritional supplements comprise a nutritional quality and a cost of a respective nutritional supplement, stored in a database.

25. The method according to claim 17, further comprising the step of providing a plurality of potential optimization procedures and selecting at least one of the optimization procedures for optimizing a proposed nutritional supplementation for the person.

26. The method according to claim 17, further comprising the step of providing nutritional supplements to the person corresponding to the proposed nutritional supplementation.

27. A method for proposing nutritional supplementation for a group of persons, comprising the steps of:
  (a) receiving health and nutritional status information relating to a group of persons;
  (b) providing information relating to a plurality of available nutritional supplements;
  (c) optimizing a proposed single nutritional supplementation regimen for the group of persons based on the health and nutritional status information and nutritional supplement information to improve a predicted health status of the group of persons by nutritional supplementation with a plurality of nutritional supplements; and (d) outputting the proposed nutritional supplementation including amounts of the plurality of nutritional supplements as a proposal.

28. The method according to claim 27, further comprising the steps of receiving economic considerations and optimizing the proposed nutritional supplementation further based on the economic considerations.

29. The method according to claim 27, further comprising the steps of receiving feedback relating to the proposed nutritional supplementation and reoptimizing to generate a revised proposed nutritional supplementation.

30. The method according to claim 27, wherein the information relating to a plurality of available nutritional supplements, the information comprising nutritional quality and cost are stored in a database.

31. A method for proposing nutritional supplementation for a person comprising the steps of:

(a) receiving health and nutritional status information relating to a person;

(b) providing information relating to a plurality of available nutritional supplements, said information being obtained by reference to an encoding on a container of a respective nutritional supplement;

(c) providing at least one optimization procedure for optimizing a proposed nutritional supplementation for the person based on the health and nutritional status information and nutritional supplement information to improve a predicted health status of the person by nutritional supplementation with a plurality of nutritional supplements;

(d) performing one or more step selected from the group consisting of:

(1) selecting one of a plurality of proposed optimization procedures for optimizing a proposed nutritional supplementation for the person; and (2) providing feedback from the person relating to the proposed nutritional supplementation and reoptimizing based on the feedback to generate a revised proposed nutritional supplementation; and (e) outputting the proposed nutritional supplementation including amounts of the plurality of nutritional supplements as a proposal.

32. The method according to claim 31, further comprising the steps of receiving economic considerations from the person and optimizing the proposed nutritional supplementation further based on the economic considerations.

33. The method according to claim 31, wherein the economic considerations comprise a budget.

34. The method according to claim 31, wherein the information relating to a plurality of available nutritional supplements, the information comprising nutritional quality and cost are stored in a database.

35. The method according to claim 31, further comprising the step of providing a plurality of potential optimization procedures and selecting at least one of the optimization procedures for optimizing a proposed nutritional supplementation for the person.

36. The method according to claim 31, further comprising the step of, after receiving approval, selling nutritional supplements to the person corresponding to the proposed nutritional supplementation.

37. The method according to claim 36, further comprising the step of receiving an approval of the proposed nutritional optimization through an electronic data transmission between a client system and a server system.

38. A method for proposing nutritional supplementation for a person comprising the steps of:

(a) receiving health and nutritional status information relating to a person;

(b) providing information relating to a plurality of available nutritional supplements, said information comprising at least nutritional value and cost of a respective nutritional supplement;

(c) optimizing a proposed nutritional supplementation for the person based on the health and nutritional status information and nutritional supplement information to improve a predicted health status of the person by nutritional supplementation with a plurality of nutritional supplements; and (d) outputting the proposed nutritional supplementation including amounts of the plurality of nutritional supplements as a proposal.

39. The method according to claim 38, further comprising the steps of receiving economic considerations from the person and optimizing the proposed nutritional supplementation further based on the economic considerations.

40. The method according to claim 39, wherein the economic considerations comprise a budget.

41. The method according to claim 38, further comprising the steps of receiving feedback from the person relating to the proposed nutritional supplementation and reoptimizing to generate a revised proposed nutritional supplementation.

* * * * *